United States Patent
Kostrzewski

(10) Patent No.: US 10,076,334 B2
(45) Date of Patent: Sep. 18, 2018

(54) SURGICAL INSTRUMENT AND METHOD FOR PERFORMING A RESECTION

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 163 days.

(21) Appl. No.: 15/294,841

(22) Filed: Oct. 17, 2016

(65) Prior Publication Data

US 2017/0027580 A1 Feb. 2, 2017

Related U.S. Application Data

(62) Division of application No. 13/798,950, filed on Mar. 13, 2013, now Pat. No. 9,492,166, which is a division
(Continued)

(51) Int. Cl.
*A61B 17/072* (2006.01)
*A61B 17/115* (2006.01)
(Continued)

(52) U.S. Cl.
CPC ........ *A61B 17/1155* (2013.01); *A61B 17/068* (2013.01); *A61B 17/072* (2013.01);
(Continued)

(58) Field of Classification Search
CPC ................ A61B 17/068; A61B 17/072; A61B 17/07207; A61B 17/07292;
(Continued)

(56) References Cited

U.S. PATENT DOCUMENTS

| 3,017,637 A | 1/1962 | Sampson |
| 4,198,982 A | 4/1980 | Fortner et al. |

(Continued)

FOREIGN PATENT DOCUMENTS

| EP | 0600182 A2 | 6/1994 |
| EP | 0698376 A2 | 2/1996 |

(Continued)

OTHER PUBLICATIONS

Canadian Office Action corresponding to counterpart Int'l Appln. No. CA 2,703,412 dated Dec. 2, 2016.
(Continued)

*Primary Examiner* — Scott A. Smith

(57) ABSTRACT

An end effector for use with a surgical instrument comprising an anvil shaft, a first anvil assembly disposed at a distal portion of the anvil shaft and a second anvil assembly mountable on the anvil shaft proximally of the first anvil assembly. Also, a method for performing a surgical procedure is provided including the steps of providing a surgical instrument including a first cartridge assembly and a first anvil assembly having an anvil shaft, approximating the first anvil assembly and first cartridge assembly and ejecting staples from the first cartridge assembly. The method further includes removing the first cartridge assembly from the tubular organ, and inserting a second anvil assembly into the tubular organ to engage the anvil shaft of the first anvil assembly and ejecting staples from a second cartridge assembly towards the second anvil assembly.

15 Claims, 11 Drawing Sheets

Related U.S. Application Data of application No. 12/770,182, filed on Apr. 29, 2010, now Pat. No. 8,418,909.

(60) Provisional application No. 61/183,201, filed on Jun. 2, 2009.

(51) Int. Cl.
  *A61B 17/068* (2006.01)
  *A61B 17/00* (2006.01)
  *A61B 17/11* (2006.01)
  *A61B 17/3205* (2006.01)
  *A61M 1/00* (2006.01)

(52) U.S. Cl.
  CPC .. *A61B 17/07207* (2013.01); *A61B 17/07292* (2013.01); *A61B 17/115* (2013.01); *A61B 17/00491* (2013.01); *A61B 17/1114* (2013.01); *A61B 17/32053* (2013.01); *A61B 2017/07214* (2013.01); *A61B 2017/07257* (2013.01); *A61B 2017/07285* (2013.01); *A61B 2017/1132* (2013.01); *A61B 2017/1142* (2013.01); *A61B 2217/005* (2013.01); *A61B 2217/007* (2013.01); *A61M 1/0058* (2013.01)

(58) Field of Classification Search
  CPC .......... A61B 17/00491; A61B 17/1114; A61B 17/115; A61B 17/1155; A61B 2017/07214; A61B 2017/07257; A61B 2017/07285; A61B 2017/00893
  USPC .......... 606/139, 143, 151, 153, 219; 227/19, 227/176.1, 179.1, 180.1, 175.1, 175.2
  See application file for complete search history.

(56) References Cited

U.S. PATENT DOCUMENTS

| | | | |
|---|---|---|---|
| 4,476,863 A * | 10/1984 | Kanshin | A61B 17/115 227/19 |
| 4,505,414 A | 3/1985 | Filipi | |
| 4,749,114 A | 6/1988 | Green | |
| 4,773,420 A | 9/1988 | Green | |
| 4,873,977 A * | 10/1989 | Avant | A61B 17/115 227/180.1 |
| 4,881,544 A | 11/1989 | Green et al. | |
| 4,930,674 A | 6/1990 | Barak | |
| 4,957,499 A * | 9/1990 | Lipatov | A61B 17/115 227/180.1 |
| 5,139,513 A * | 8/1992 | Segato | A61B 17/115 227/179.1 |
| 5,188,636 A | 2/1993 | Fedotov | |
| 5,197,649 A * | 3/1993 | Bessler | A61B 17/1114 227/156 |
| 5,222,963 A | 6/1993 | Brinkerhoff et al. | |
| 5,250,058 A | 10/1993 | Miller et al. | |
| 5,344,059 A * | 9/1994 | Green | A61B 17/115 227/179.1 |
| 5,346,501 A | 9/1994 | Regula et al. | |
| 5,445,644 A * | 8/1995 | Pietrafitta | A61B 17/115 227/175.1 |
| 5,470,008 A | 11/1995 | Rodak | |
| 5,588,579 A | 12/1996 | Schnut et al. | |
| 5,758,814 A | 6/1998 | Gallagher et al. | |
| 5,816,471 A | 10/1998 | Plyley et al. | |
| 5,833,695 A | 11/1998 | Yoon | |
| 6,503,259 B2 * | 1/2003 | Huxel | A61B 17/0643 227/179.1 |
| 6,673,088 B1 | 1/2004 | Vargas et al. | |
| 6,959,851 B2 | 11/2005 | Heinrich | |
| 7,128,748 B2 * | 10/2006 | Mooradian | A61B 17/115 606/151 |
| 7,179,267 B2 * | 2/2007 | Nolan | A61B 17/1114 227/175.1 |
| 7,237,708 B1 | 7/2007 | Guy et al. | |
| 7,285,125 B2 * | 10/2007 | Viola | A61B 17/11 128/898 |
| 7,303,106 B2 | 12/2007 | Milliman et al. | |
| 7,527,185 B2 * | 5/2009 | Harari | A61B 17/0643 227/179.1 |
| 7,942,890 B2 * | 5/2011 | D'Agostino | A61B 17/072 606/153 |
| 8,123,766 B2 * | 2/2012 | Bauman | A61B 17/072 227/180.1 |
| 8,205,782 B2 * | 6/2012 | Harari | A61B 17/0643 227/179.1 |
| 8,276,802 B2 | 10/2012 | Kostrzewski | |
| 8,418,909 B2 | 4/2013 | Kostrzewski | |
| 8,435,203 B2 * | 5/2013 | Viola | A61B 17/0643 604/164.01 |
| 8,631,993 B2 | 1/2014 | Kostrzewski | |
| 8,746,531 B2 | 6/2014 | Wenchell et al. | |
| 8,821,523 B2 * | 9/2014 | Heinrich | A61B 17/00491 227/175.1 |
| 8,875,970 B2 * | 11/2014 | Viola | A61B 17/115 227/175.1 |
| 8,905,286 B2 | 12/2014 | Kostrzewski | |
| 9,084,601 B2 | 7/2015 | Moore et al. | |
| 9,211,120 B2 | 12/2015 | Scheib et al. | |
| 9,271,799 B2 | 3/2016 | Shelton, IV et al. | |
| 9,492,166 B2 * | 11/2016 | Kostrzewski | A61B 17/115 |
| 2005/0021053 A1 | 1/2005 | Heinrich | |
| 2005/0205640 A1 * | 9/2005 | Milliman | A61B 17/1155 227/176.1 |
| 2006/0085033 A1 * | 4/2006 | Criscuolo | A61B 17/00491 606/219 |
| 2006/0085034 A1 * | 4/2006 | Bettuchi | A61B 17/115 606/219 |
| 2006/0135992 A1 * | 6/2006 | Bettuchi | A61B 17/072 606/219 |
| 2007/0034668 A1 | 2/2007 | Holsten et al. | |
| 2008/0190990 A1 | 8/2008 | Holsten et al. | |
| 2008/0277450 A1 | 11/2008 | Dudai | |
| 2009/0005808 A1 | 1/2009 | Hess et al. | |
| 2009/0132021 A1 | 5/2009 | Shifrin et al. | |
| 2009/0302092 A1 | 12/2009 | Kasvikis et al. | |
| 2010/0065606 A1 | 3/2010 | Stopek | |
| 2010/0072258 A1 | 3/2010 | Farascioni et al. | |
| 2010/0213238 A1 | 8/2010 | Farascioni et al. | |
| 2010/0301098 A1 | 12/2010 | Kostrzewski | |
| 2011/0087279 A1 | 4/2011 | Shah et al. | |

FOREIGN PATENT DOCUMENTS

| | | |
|---|---|---|
| EP | 2258282 A2 | 12/2010 |
| EP | 2272442 A1 | 1/2011 |
| JP | 2010279690 A | 12/2010 |
| JP | 2011015962 A | 1/2011 |
| WO | 2009143331 A1 | 11/2009 |

OTHER PUBLICATIONS

European Search Report for EP 11178544 dated Sep. 29, 2011.
European Search Report for EP 11250468.3 dated Aug. 10, 2011.
European Search Report dated Jan. 9, 2015 issued in EP Appln. No. 10251021.
Canadian Office Action corresponding to counterpart Int'l Appln. No. CA 2,703,412, dated Mar. 3, 2016.
Australian Examination Report dated Mar. 10, 2015, issued in Australian Appln. No. 2010201947.
Australian Examination Report No. 1 corresponding to counterpart Int'l Appln. No. AU 2015261713 dated Aug. 11, 2016.

* cited by examiner

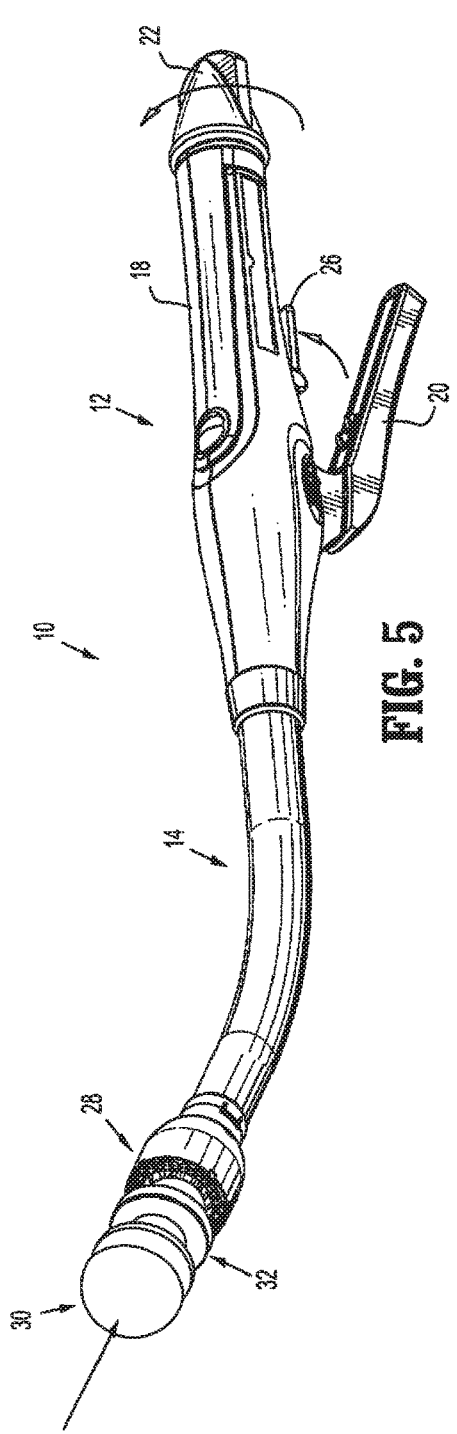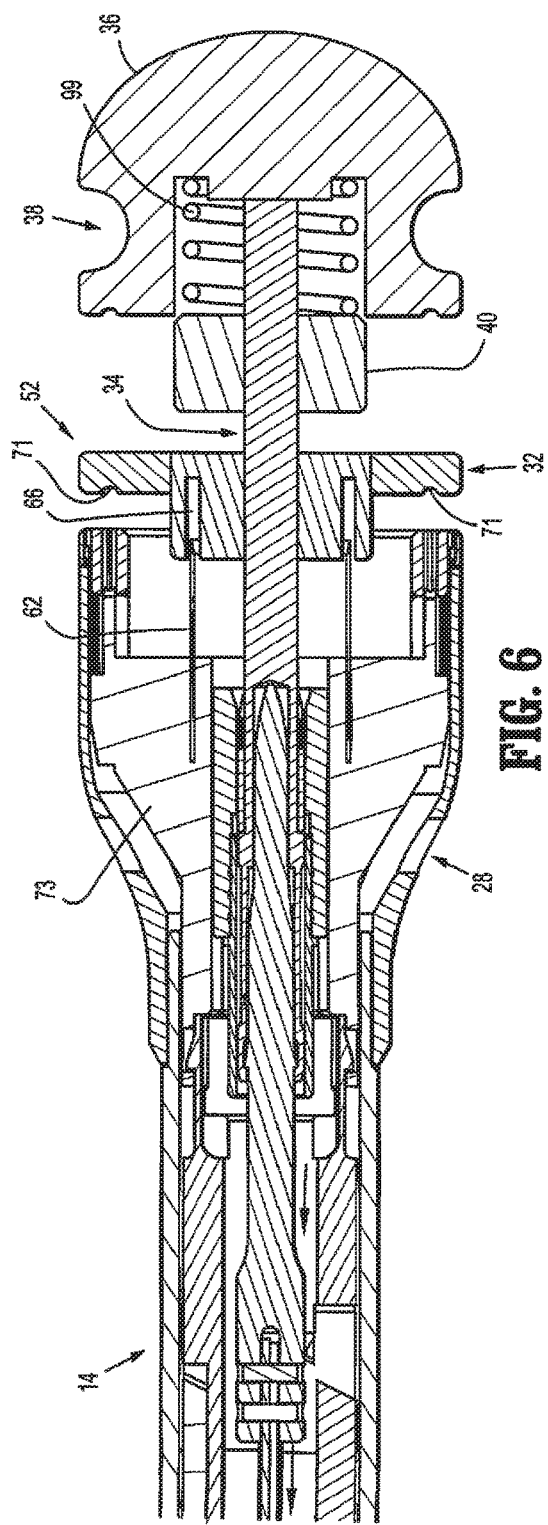

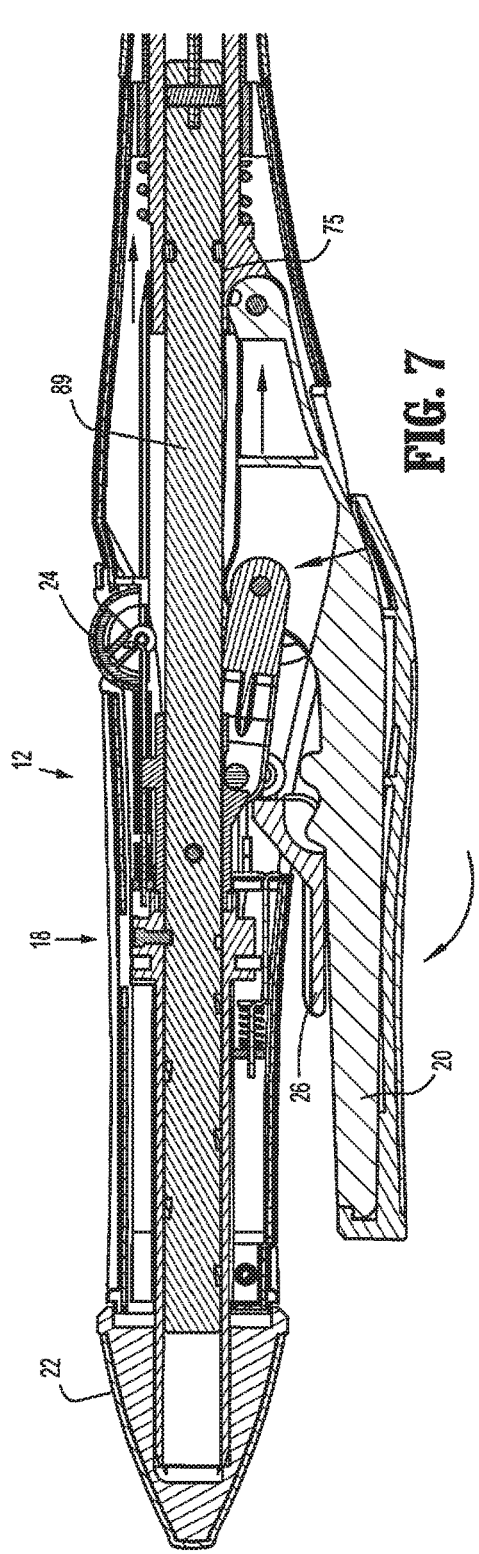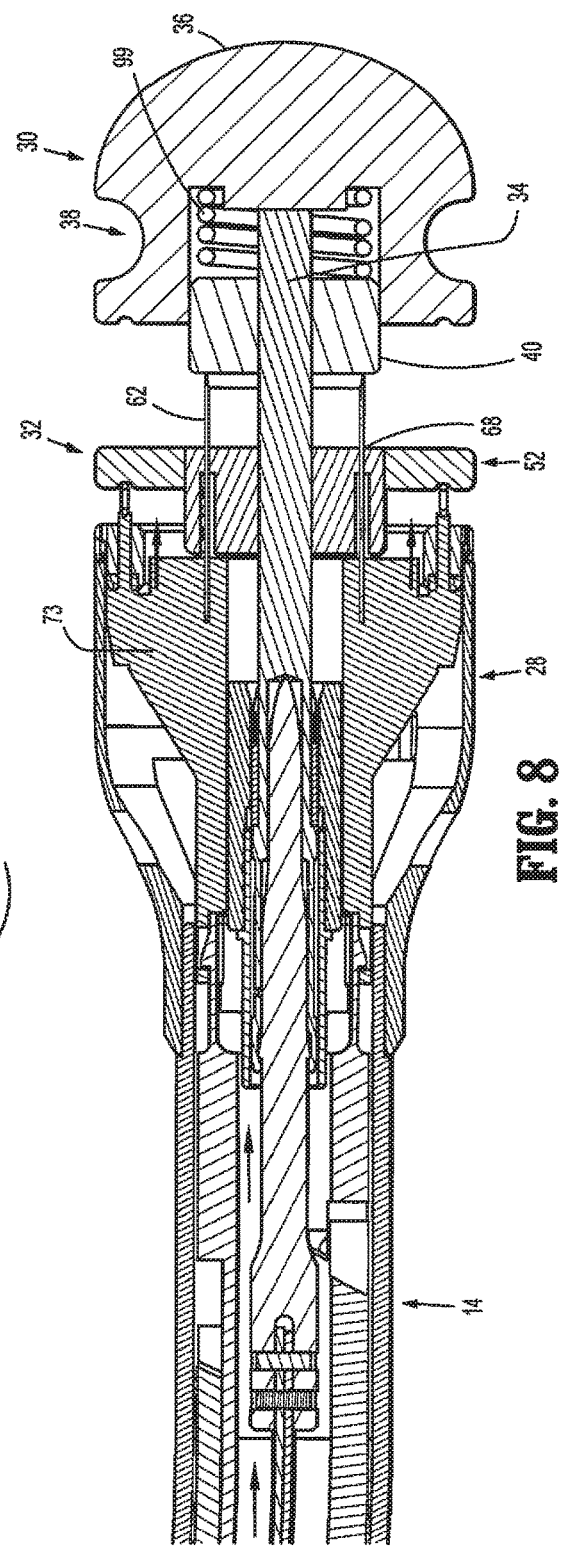

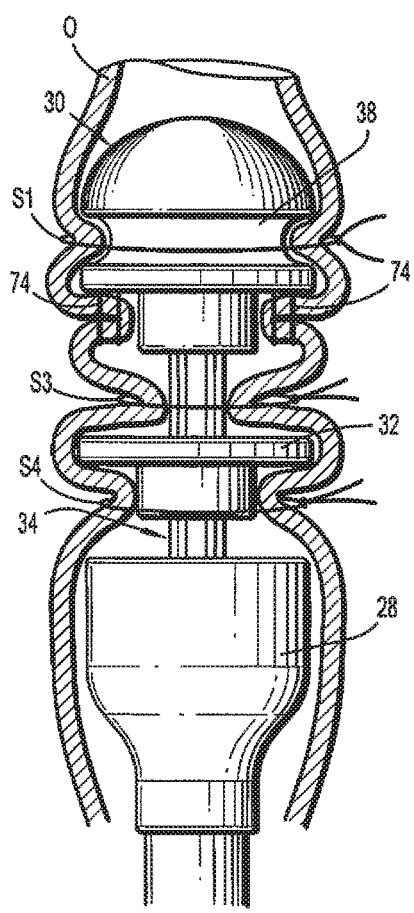
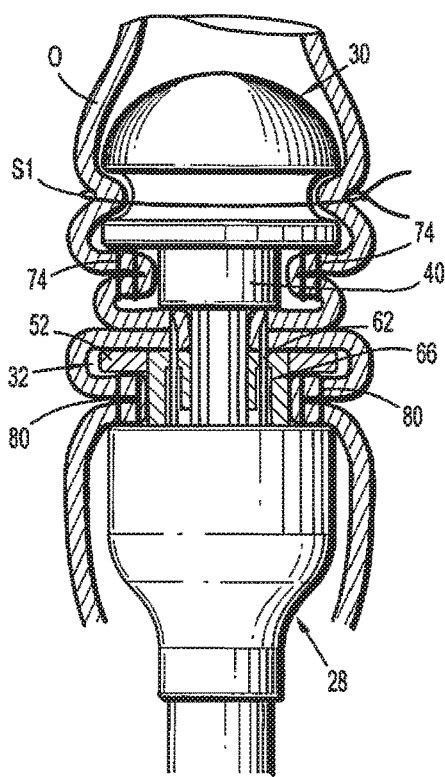
FIG. 13
FIG. 14

SURGICAL INSTRUMENT AND METHOD FOR PERFORMING A RESECTION

CROSS-REFERENCE TO RELATED APPLICATIONS

This application is a Divisional of U.S. patent application Ser. No. 13/798,950 filed Mar. 13, 2013, now U.S. Pat. No. 9,492,166, which is a Divisional of U.S. patent application Ser. No. 12/770,182 filed Apr. 29, 2010, now U.S. Pat. No. 8,418,909, which claims benefit of and priority to U.S. Provisional Application No. 61/183,201 filed Jun. 2, 2009, and the disclosures of each of the above-identified applications are hereby incorporated by reference in their entirety.

BACKGROUND

Technical Field

The present disclosure relates generally to a surgical instrument and, more specifically, to a surgical instrument for clamping, cutting, and/or joining tissue.

Background of Related Art

Certain surgical stapling instruments are used for applying rows of staples through compressed living tissue. These surgical stapling instruments are employed, for example, for fastening tissue or organs prior to transection or resection or during anastomoses. In some cases, these surgical stapling instruments are utilized for occluding organs in thoracic and abdominal procedures.

Typically, such surgical stapling instruments include an anvil assembly, a cartridge assembly for supporting an array of surgical staples, an approximation mechanism for approximating the cartridge and anvil assemblies, and a firing mechanism for ejecting the surgical staples from the cartridge assembly.

In use, a surgeon initially advances an alignment pin assembly and subsequently approximates the anvil and cartridge assemblies. Next, the surgeon can fire the instrument to the instrument to place staples in tissue. Optionally, the surgeon may use the same instrument or a separate device to cut the tissue adjacent or between the row(s) of staples.

SUMMARY

The present disclosure in one aspect relates to an end effector for use with a surgical instrument comprising an anvil shaft, a first anvil assembly disposed at a distal portion of the anvil shaft, and a second anvil assembly mountable on the anvil shaft proximally of the first anvil assembly.

Preferably, the anvil assembly and anvil shaft are aligned by key slots.

In one embodiment, the first anvil assembly has a first plurality of anvil pockets arranged in a substantially annular row to deform fasteners fired from a first fastener cartridge and the second anvil assembly has a second plurality of anvil pockets arranged in a substantially annular row to deform fasteners fired from a second fastener cartridge.

Preferably, each of the first anvil assembly and the second anvil assembly is slidable in response to movement of the anvil shaft. The second anvil assembly can include a weakened portion that is configured to break when a knife moves therethrough and the first anvil assembly can have a knife receiving portion for embedding the knife when the knife moves through the second anvil assembly.

In some embodiments, the second anvil assembly is mountable to the anvil shaft after fasteners are deformed by the first anvil assembly.

In some embodiments, the anvil shaft is removably mountable to a surgical instrument having a cartridge containing a plurality of fasteners and an actuator for firing the fasteners from the cartridge.

In another aspect, the present disclosure relates to a method for performing a resection. This method includes the steps: providing a surgical instrument including a first cartridge assembly and a first anvil assembly having an anvil shaft; inserting the first anvil assembly into a tubular organ; approximating the first anvil assembly toward the first cartridge assembly; ejecting staples from the first cartridge assembly towards the first anvil assembly; removing the first cartridge assembly from the tubular organ such that the first cartridge assembly operatively disengages the anvil shaft of the first anvil assembly; inserting a second anvil assembly into the tubular organ such that the second anvil assembly operatively engages the anvil shaft of the first anvil assembly; and ejecting staples from a second cartridge assembly towards the second anvil assembly.

The method can further include the step of inserting the first cartridge assembly into the tubular organ such that the first cartridge assembly operatively engages the first anvil assembly prior to the step of approximating the first cartridge.

The method can further include the step of inserting a second cartridge assembly into the tubular organ such that the second cartridge assembly operatively engages the second anvil assembly prior to the step of approximating the second cartridge.

BRIEF DESCRIPTION OF THE DRAWINGS

Various embodiments of the presently disclosed surgical instruments and methods are disclosed herein with reference to the drawings, wherein:

FIG. 5 is a perspective view of the surgical instrument shown in FIGS. 1 and 2, illustrating a stage of operation of said surgical instrument;

FIG. 6 is a longitudinal cross-sectional view of a distal portion of the surgical instrument shown in FIG. 1, depicting another stage of operation of said surgical instrument;

FIG. 7 is a longitudinal cross-sectional view of the handle assembly shown in FIG. 3 being actuated;

FIG. 8 is a longitudinal cross-sectional view of the end effector shown in FIG. 4 shown being moved to the approximated position;

FIG. 13 is a longitudinal cross-sectional view of the tubular organ shown in FIG. 9 with the first anvil assembly, the second anvil assembly, and the cartridge assembly of the surgical instrument of FIG. 1 positioned therein, showing the surgical instrument before approximation and firing;

FIG. 14 is a longitudinal cross-sectional view of the tubular organ shown in FIG. 9 with the first anvil assembly, the second anvil assembly, and the cartridge assembly of the surgical instrument of FIG. 1 positioned therein, showing the surgical instrument after it has been approximated and fired.

DETAILED DESCRIPTION OF THE EMBODIMENTS

Figure 1:
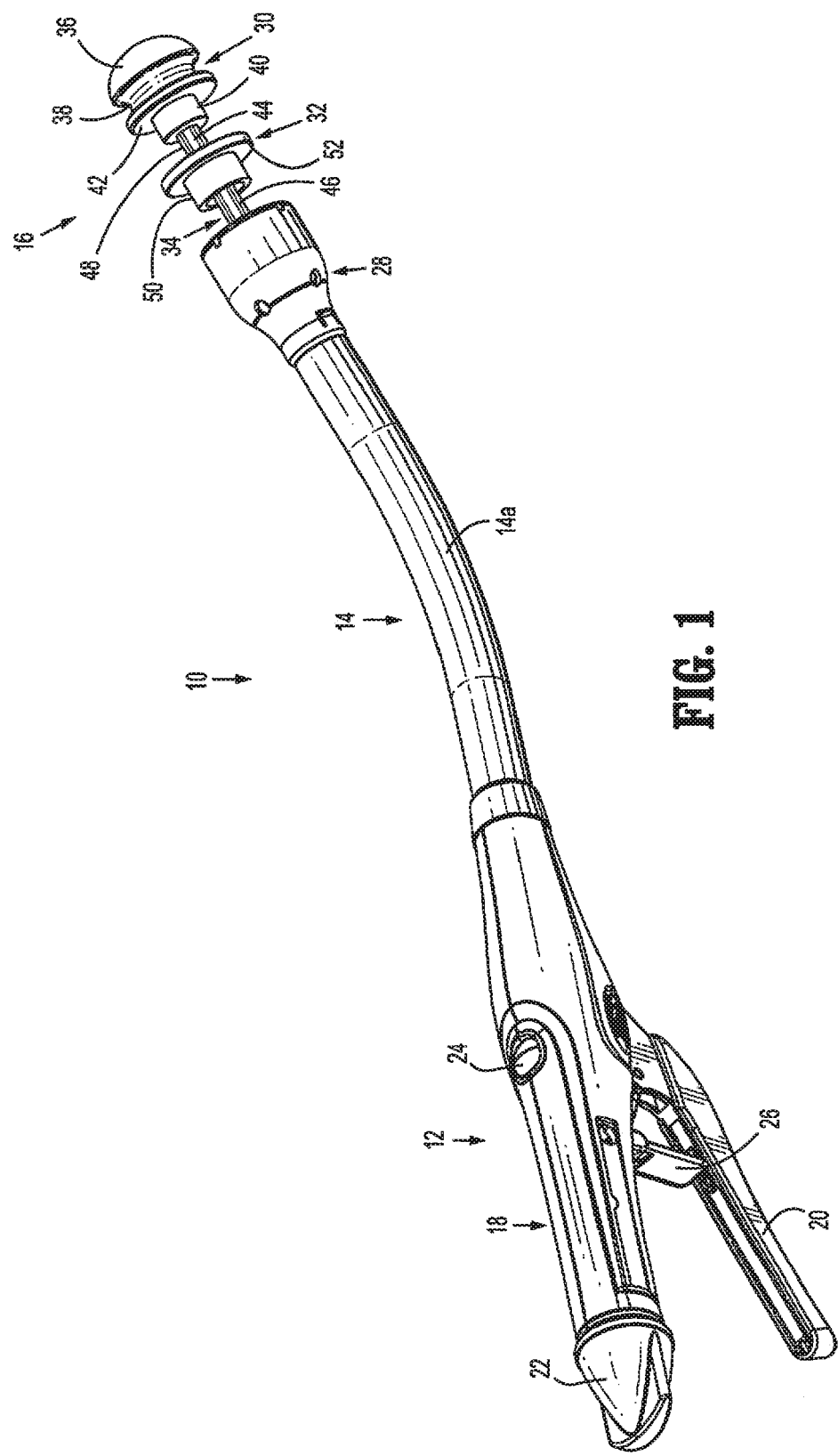
FIG. 1 is a perspective view of a surgical instrument according to an embodiment of the present disclosure, the instrument used to fire a second set of fasteners.

Embodiments of the presently disclosed surgical instrument and method are described in detail with reference to the drawings, wherein like reference numerals designate corresponding elements in each of the several views. In the description that follows, the term "proximal" refers to the end or portion of the surgical instrument closer to the clinician, whereas the term "distal" refers to the end or portion of the surgical instrument further away from the clinician.

Figure 2:
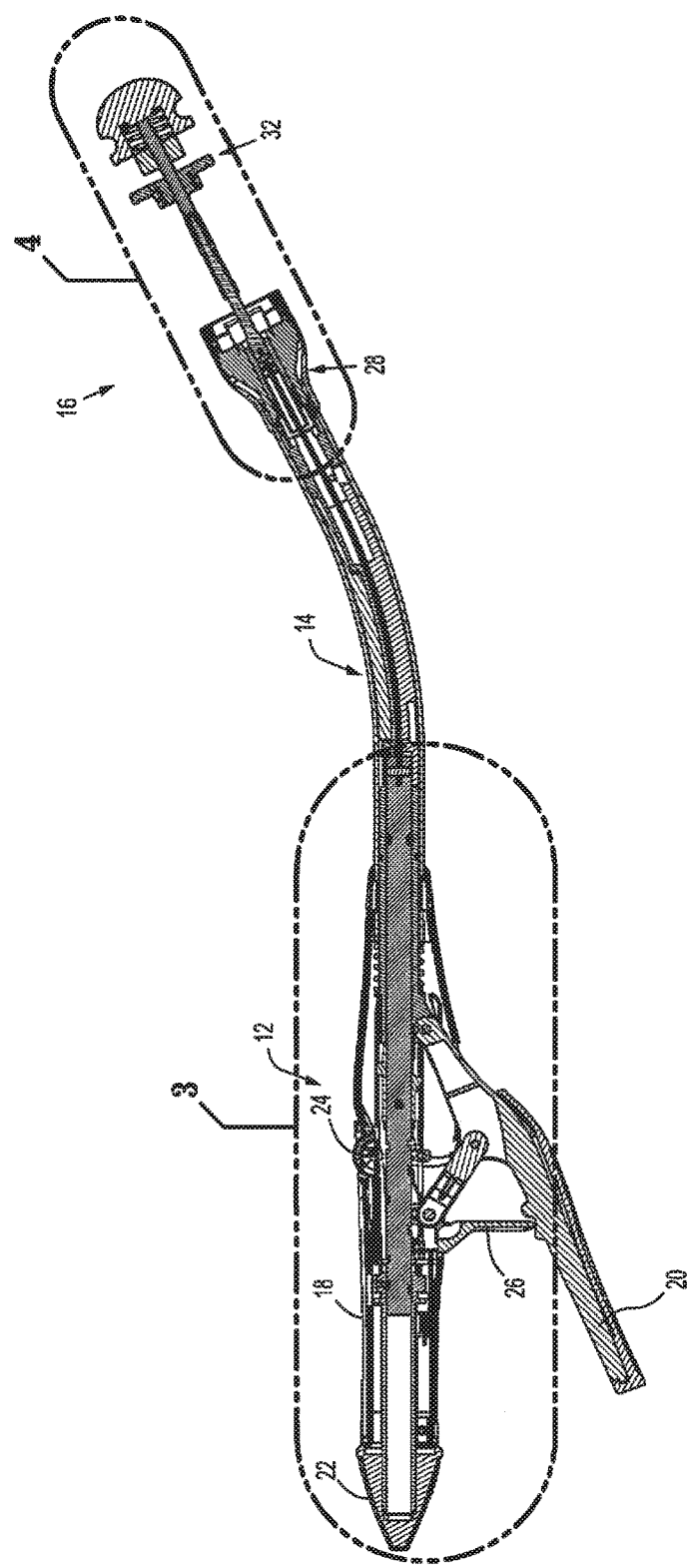
FIG. 2 is a longitudinal cross-sectional view of the surgical instrument shown in FIG. 1.
Figure 3:
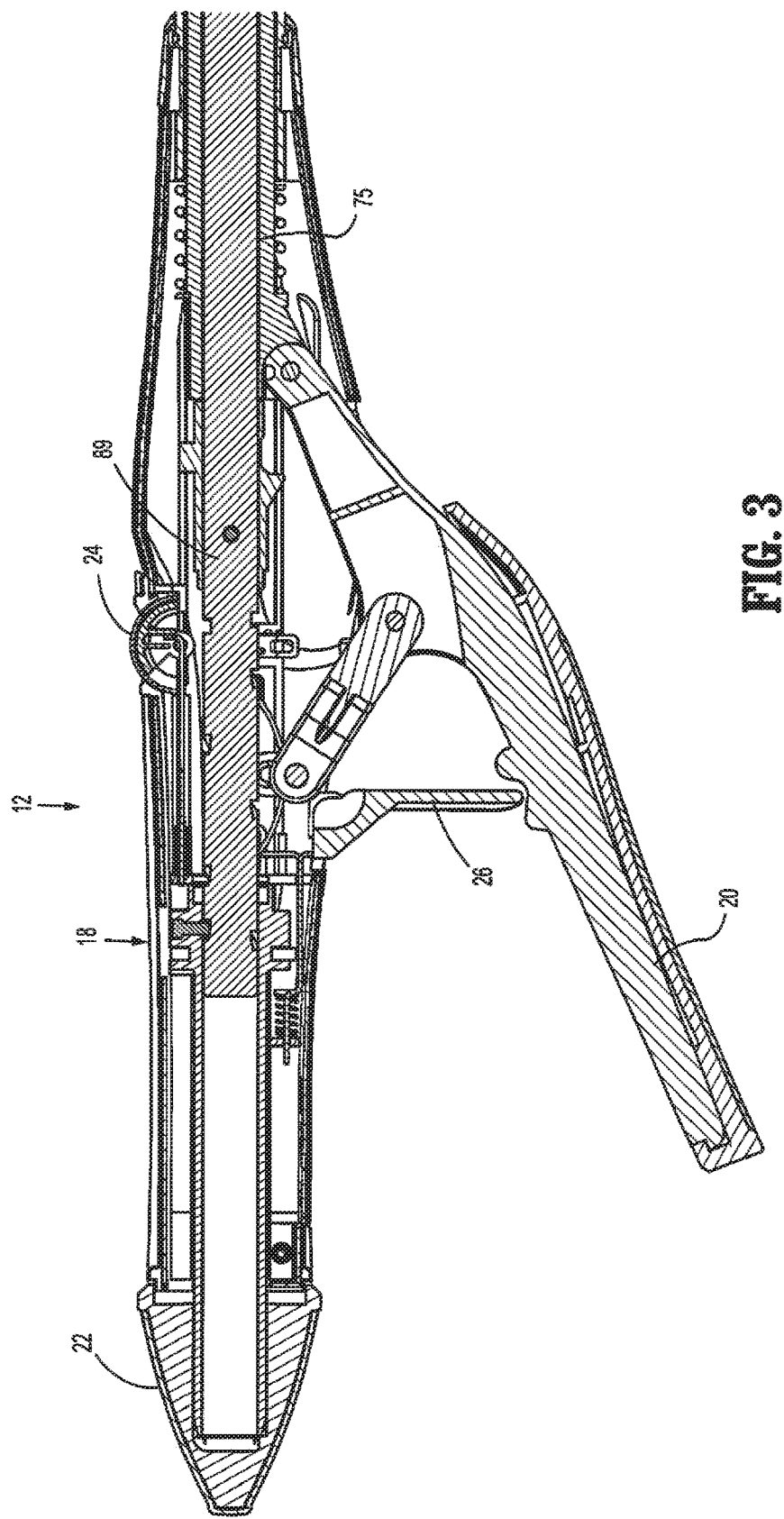
FIG. 3 is a longitudinal cross-sectional view of a handle assembly of the surgical instrument shown in FIGS. 1 and 2, taken around section 3 of FIG. 2.
Figure 4:
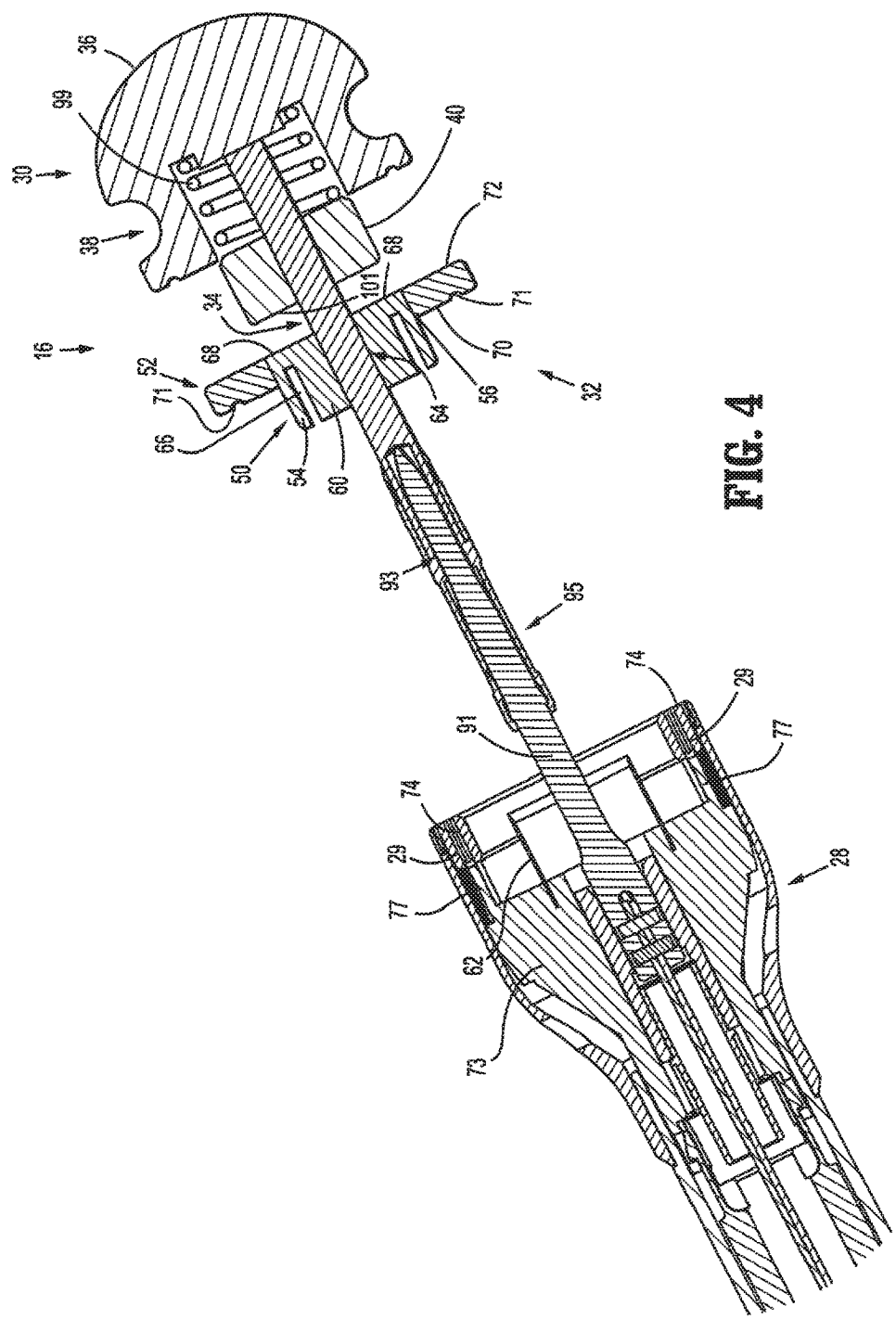
FIG. 4 is a longitudinal cross-sectional view of a distal portion of the surgical instrument shown in FIGS. 1 and 2, taken around section 4 of FIG. 2.
Figure 4A:
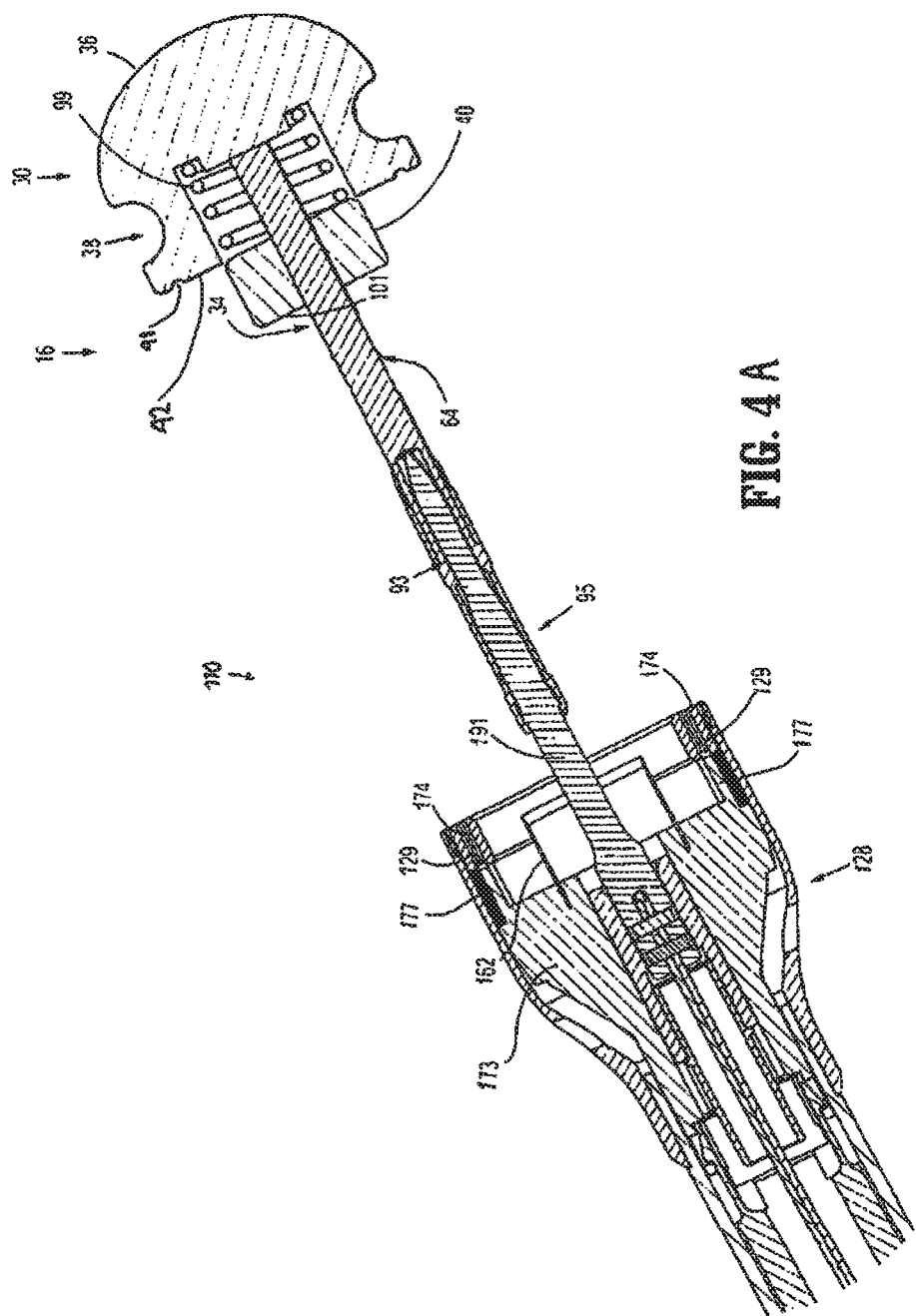
FIG. 4A is a longitudinal cross-sectional view of a distal portion of another surgical instrument used to fire the first set of fasteners.

FIGS. 1 and 2 illustrate an embodiment of the presently disclosed surgical instrument 10 when both first and second anvil assemblies are positioned on the anvil shaft. As will be described in more detail below, a first instrument is used for firing a first set of fasteners with respect to a first anvil assembly. The first instrument is then separated from the anvil assembly and removed from the body. The second anvil assembly is then inserted onto the anvil shaft of the first anvil assembly and a second instrument is utilized to fire a second set of fasteners with respect to the second anvil assembly. FIG. 1 illustrates the second instrument used to fire fasteners against second anvil assembly 32; FIG. 4A illustrates a portion of the first instrument used to fire fasteners against first anvil assembly 30. As shown in FIGS. 1 and 2, the first anvil assembly 30 is positioned distally of the second anvil assembly 32.

In the interest of brevity, the present disclosure focuses on end effectors for the disclosed second surgical instrument 10. U.S. Pat. No. 7,303,106, the entire contents of which are hereby incorporated by reference, describes in detail the structure and operation of an embodiment of surgical instrument 10.

Turning first to the second surgical instrument and with reference to FIGS. 1 and 2, in general, the second surgical instrument 10 includes a handle assembly 12, an elongated central body portion 14 including a curved elongated outer tube 14a, and an end effector or distal head or end portion 16. Elongated central body portion 14 extends distally from handle assembly 12 and operatively couples end effector 16 to handle assembly 12. In operation, end effector 16 fires fasteners into anvil assembly 32, deploys a cutting device 62 (FIG. 8), or both, upon actuation of handle assembly 12.

Handle assembly 12 includes a stationary handle 18, a firing trigger 20, a rotatable approximation knob 22 and an indicator 24. In certain embodiments, stationary handle 18 is made of a thermoplastic, such as polycarbonate. In other embodiments, stationary handle 18 is formed of an elastomeric material. Stationary handle 18 may nevertheless be formed of any suitable material. In some embodiments, stationary handle 18 has a hollow body that houses internal components of handle assembly 12. U.S. Pat. No. 7,303,106, the entire contents of which have already been incorporated by reference, describes in detail the internal components of handle assembly 12.

Handle assembly 12 further includes a trigger lock 26 for preventing, or at least minimizing, the risk of inadvertently firing surgical instrument 10. In the embodiment depicted in FIG. 1, trigger lock 26 is pivotally mounted to stationary handle 18. During use, trigger lock 26 is configured to move relative to stationary handle 18 between a locked position and an unlocked position. In the locked position, trigger lock 26 engages firing trigger 20 and precludes, or at least hinders, movement of firing trigger 20 with respect to stationary handle 18. In the unlocked position, trigger lock 26 allows firing trigger 20 to move or pivot relative to stationary handle 18. Stationary handle 18 additionally includes an indicator 24 to indicate to a clinician whether end effector 16 is approximated and/or is ready to be fired. In some embodiments, indicator 24 has a bulbous or convex shape extending outwardly from a top surface of stationary handle 18. Stationary handle 18 also includes approximation knob 22 operatively coupled to end effector 16. Approximation knob 22 is configured to rotate with respect to stationary handle 18. A rotation of approximation knob 22 relative to stationary handle 18 causes end effector 16 to move between an open position (FIG. 4) and an approximated position (FIG. 6).

End effector 16 generally includes a cartridge assembly 28, a first anvil assembly 30 having an anvil shall 34 and a second anvil assembly 32 slidably mountable on the anvil shaft 34. Cartridge assembly 28 houses an array of fasteners, such as staples, and is configured to eject those fasteners in a distal direction into engagement with anvil pockets on second anvil assembly 32 (As noted above, anvil assembly 30 receives fasteners of a different surgical instrument). Cartridge assembly 28 includes slots 29 (FIG. 4) dimensioned to receive the fasteners 74 (FIG. 4). Slots 29 may be arranged in one or more substantially annular rows or in any other suitable configuration.

Turning now to the first anvil assembly 30, anvil assembly 30 includes a blunt or round distal head 36 and a tubular member 40 and is configured to receive fasteners of the first surgical instrument of FIG. 4A. More specifically, with reference to FIGS. 1 and 4A, tubular member 40 is movable with respect to distal head 36. In some embodiments, a biasing member, such as a spring 99, biases tubular member 40 in a proximal direction. Tubular member 40 defines a lumen configured to receive anvil shaft 34. Distal head 36 includes a circumferential groove 38 adapted to receive a purse string suture. Groove 38 surrounds distal head 36 and may have a concave configuration. Distal head 36 further includes a proximal surface 42 located proximally relative to groove 38. Proximal surface 42 has a plurality of anvil pockets 41 adapted to receive and deform fasteners 174 ejected from cartridge assembly 128 of the first surgical instrument. In disclosed embodiments, proximal surface 42 is made of a metal, such as stainless steel or aluminum. In some embodiments, these pockets are arranged in one or more substantially annular rows on proximal surface 42. Other arrangements are contemplated to correspond to arrangements of the fastener slots 129.

Anvil shaft 34 extends proximally from first anvil assembly 30 and has a proximal end 46 and a distal end 44. Distal end 44 of anvil shaft 34 is attached to first anvil assembly 30, whereas proximal end 46 of anvil shaft 34 is configured to be releasably coupled to the rod extending from the cartridge assembly 128. Anvil shaft 34 additionally includes longitudinal keys 48 extending between proximal end 46 and distal end 44. Longitudinal keys 48 are configured to engage second anvil assembly 32 to guide the translation of second anvil assembly 32 along anvil shaft 34. In use, longitudinal keys 48 block, or at least hinder, rotation of second anvil assembly 32 relative to anvil shaft 34.

Figures 11, 12:
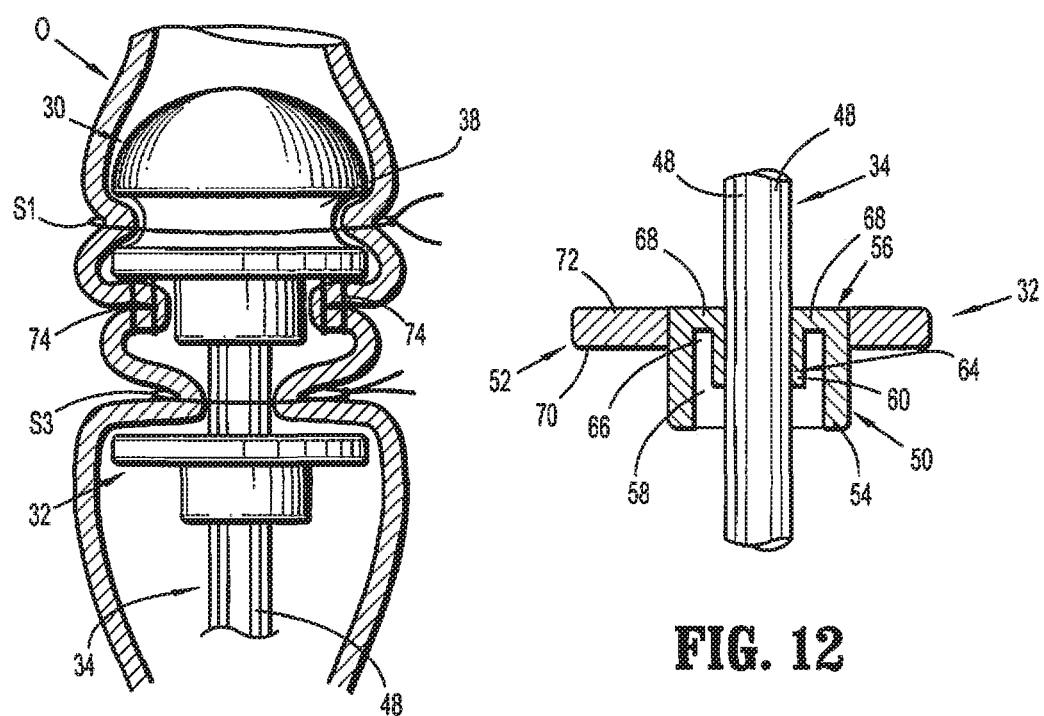
FIG. 11 is a longitudinal cross-sectional view of the tubular organ shown in FIG. 9 with the first anvil assembly and a second anvil assembly positioned therein, and a pursestring suture wrapped around a portion of the tubular member located between the first anvil assembly and the second anvil assembly.
FIG. 12 is a perspective view of an anvil shaft and the second anvil assembly shown in FIG. 11 in cross-section.

Turning now to second anvil assembly 32, configured for use with the second surgical instrument of FIG. 1, and with reference to FIGS. 1, 4 and 12, second anvil assembly 32 includes a tubular member 50 and a ring 52 disposed around tubular member 50. Tubular member 50 has a proximal end 54 and a distal end 56. In addition, tubular member 50 includes a guide 60 adapted to guide a knife or any suitable cutting device 62 deployed from cartridge assembly 28 of instrument 10. In certain embodiments, guide 60 has a tubular shape and defines a longitudinal opening 64 configured to slidably receive anvil shaft 34. In some embodiments, guide 60 includes one or more slots (not shown) disposed along an inner surface thereof. The slots (not shown) of guide 60 are adapted to engage longitudinal keys 48 of anvil shaft 34. The engagement between longitudinal keys 48 and the slots of guide 60 facilitate axial translation of second anvil assembly 32 along anvil shaft 34, while precluding, or at least inhibiting, rotation of second anvil assembly 32 relative to anvil shaft 34. Guide 60 defines an annular space 66. Annular space 66 is dimensioned to receive cutting device 62 and is disposed adjacent a weakened or breakable portion 68 of tubular member 50. Weakened portion 68 may be made of a polymer or any material suitable to break upon passage of cutting device 62 therethrough. Cutting device 62 is made of a metal, such as stainless steel or aluminum, or any material suitable to cut tissue. Weakened portion 68 is disposed adjacent distal end 56 of tubular member 50. The break away portion of anvil assembly 32 can pass through the body or otherwise be captured and removed from the body.

Ring 52 is positioned around distal end 56 of tubular member 50 and has a proximal surface 70 and a distal surface 72. In some embodiments, ring 52 is made of metal, such as stainless steel or aluminum, or any other material suitable to deform fasteners 74 ejected from cartridge assembly 28. In some embodiments, proximal surface 70 of ring 52 includes fastener deforming pockets or concavities 71 configured to deform fasteners 74 deployed from cartridge assembly 28 of the second surgical instrument 10 upon contact with the pockets.

With reference to FIGS. 3-8, firing trigger 20 is operatively coupled to a fastener pusher 73 (FIGS. 4 and 6) positioned inside first cartridge assembly 28. In several embodiments, surgical instrument 10 includes a firing link assembly 75 (FIG. 3) operatively interconnecting firing trigger 20 and fastener pusher 73. Firing link assembly 75 extends from handle assembly 12 to cartridge assembly 28. In operation, actuation of firing trigger 20 causes a distal translation of fastener pusher 73 due to distal translation of firing link assembly 75. Fastener pusher 73 includes one or more fingers 77 (FIG. 4) dimensioned to be received in slots 29 of first cartridge assembly 28. When fastener pusher 73 moves distally in response to an actuation of firing trigger 20, fingers 77 move distally toward slots 29 and urge fasteners 74 toward second anvil assembly 32.

With continued reference to FIGS. 3-8, surgical instrument 10 further includes an approximation link assembly 89 operatively coupling approximation knob 22 to anvil shaft 34. As seen in FIG. 4, approximation link assembly 89 includes a rod or shaft 91 protruding distally from cartridge assembly 28. Rod 91 is disposed in mechanical cooperation with anvil shaft 34 (e.g., in a friction-fit relationship). In certain embodiments, anvil shaft 34 defines a longitudinal opening 93 dimensioned to receive rod 91. Longitudinal opening 93 extends through a proximal portion 95 of anvil shaft 34. In operation, a rotation of approximation knob 22 effects a translation of approximation link assembly 89. Rotation of knob 22 rotates an internal screw which is operatively connected to link assembly 89 via pin 87 to thereby move link assembly 89 in a proximal or distal direction, depending on the direction of rotation of knob 22. As approximation link assembly 89 translates, rod 91 moves proximally or distally as it is connected to link assembly 89 via pins 92. Since rod 91 is coupled to anvil shaft 34, movement of rod 91 causes anvil shaft 34 to move as well. While anvil shaft 34 moves, second anvil assembly 32 correspondingly moves in a distal or proximal direction.

It should be noted that similarly, when rod 191 of first instrument 110 of FIG. 4A moves, it moves anvil shaft 34 to move first anvil assembly 30 in a proximal or distal direction. That is, a user may approximate first anvil assembly 30 to cartridge assembly 128 by rotating an approximation knob (similar to approximation knob 122 of FIG. 1) in a first direction (e.g., clockwise). In response, the approximation link assembly moves proximally and urges rod 191 in a proximal direction. As rod 191 moves proximally, anvil shaft 34 translates proximally and pulls first anvil assembly 30 toward cartridge assembly 128 from an open position to an approximated position, as described in detail below.

Referring back to the second instrument, as shown in FIG. 4, cartridge assembly 28 of the second surgical instrument further may include a knife blade, or any suitable cutting device 62 movable between a retracted or proximal position and a deployed or distal position. In some embodiments, knife 62 is operatively connected to fastener pusher 73 and may have an annular configuration or shape. Knife 62 may be made of a metal, such as stainless steel. In the retracted position, knife 62 is positioned within cartridge assembly 28. In the deployed position, knife 62 is at least partially positioned outside of cartridge assembly 28. While knife 62 moves between the retracted and deployed positions, at least a portion of knife 62 passes through an annular space 66 defined in second anvil assembly 32 and through breakable annular portion 68, as discussed below.

With continued reference to FIG. 4, second anvil assembly 32 is slidably positioned on anvil shaft 34 and includes annular space 66 defined in tubular portion 50. Annular space 66 surrounds longitudinal opening 64 and is dimensioned to receive knife 62. During use, annular space 66 guides the translation of knife 62 through second anvil assembly 32. Second anvil assembly 32, as discussed above, also includes a breakable or weakened annular portion 68 substantially axially aligned with annular space 66. Breakable annular portion 68 may be made of ceramic, plastic, or any other suitable material and is positioned distally of annular space 66. Breakable annular portion 68 is made of a material that can be broken by knife 62 during the firing process. As knife 62 moves from the retracted position to the deployed position, knife 62 passes through annular space 66 of second anvil assembly 32 and then breaks breakable annular portion 68 of second anvil assembly 32. After knife 62 breaks through breakable annular portion 68, knife 62 continues moving toward first anvil assembly 30 wherein it becomes embedded. More specifically, first anvil assembly 30, coupled to anvil shaft 34, includes tubular portion 40 having a proximal surface 101. Proximal surface 101 of tubular portion 40 serves as a knife cutting target. As such, proximal surface 101 of tubular portion 40 receives knife 62 and stops further distal translation of knife 62 during the firing process as the knife becomes embedded therein. The anvil assembly 30 can include a cut ring.

Cutting device 62 is configured to move between a proximal or retracted position and a distal or deployed position. In the retracted position, cutting device 62 is positioned inside cartridge assembly 28, whereas, in the deployed position, cutting device 62 is at least partially positioned outside of cartridge assembly 62. In some embodiments, cutting device 62 moves from the retracted position to the deployed position concomitantly with distal advancement (firing of) the fasteners upon actuation of handle assembly 12. In other embodiments, cutting device 62 can be selectively advanced independently of the fasteners stored in cartridge assembly 28. In these embodiments, the clinician can eject the fasteners housed in cartridge assembly 28, while maintaining cutting device 62 in the retracted position. Subsequently, cutting device 62 would be actuated.

With reference to FIGS. 9-15, the method of use of the surgical instruments disclosed herein to cut, fasten, and/or join tissue in a number of surgical procedures is disclosed. For example, surgical instrument 10 may be employed in a lower anterior resection where it is desirable to clamp an upper portion of the bowel for cleaning the rectum prior to resection and joining the two tissue sections.

Figure 9:
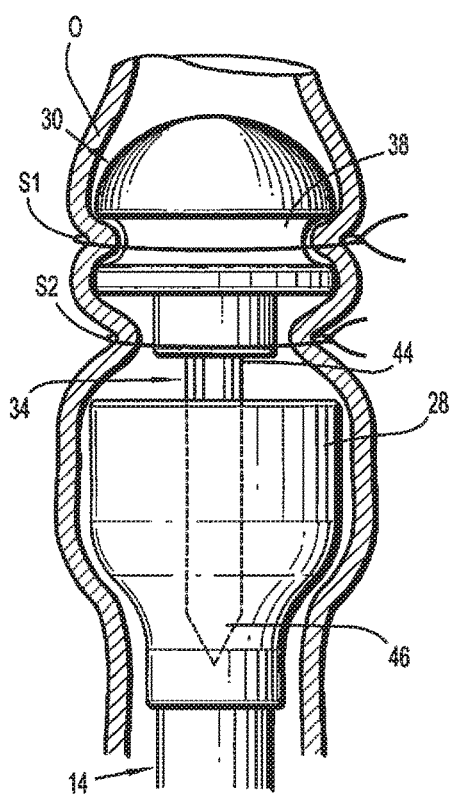
FIG. 9 is a longitudinal cross-sectional view of a tubular organ with a cartridge assembly and a first anvil assembly of the surgical instrument of FIG. 4A positioned therein, showing the first anvil assembly secured inside the tubular organ with a pursestring suture.

In one exemplary procedure, a clinician inserts first anvil assembly 30 along with anvil shaft 34 into a tubular vessel or organ "O", such as the intestine (see FIG. 9). First anvil assembly 30 may be inserted into the intestine through a patient's anus. Irrespective of the insertion method, first anvil assembly 30 may be positioned, for example, adjacent a tumor. In particular, first anvil assembly 30 may be placed just distally of the tumor. After placing the first anvil assembly 30 in the desired site, the clinician fixes the position of first anvil assembly 30 relative to tubular organ "O." To fix the position of first anvil assembly 30, the clinician may wrap a purse string suture "S1" around a portion of tubular organ located around groove 38, as shown in FIG. 9. Then, the clinician tightens string "S1" to secure first anvil assembly 30 within tubular organ "O." Alternatively, the clinician secures first anvil assembly 30 inside tubular organ "O" with a mechanical clamp.

Once first anvil assembly 30 has been secured to tubular organ "O," the clinician inserts the first surgical instrument 110 of FIG. 4A containing cartridge assembly 128 into tubular organ "O" such that cartridge assembly 128 operatively engages first anvil assembly 30. Specifically, the clinician advances cartridge assembly 128 through tubular organ "O" and cartridge assembly 128 is operatively connected to anvil shaft 34 via rod or (anvil retainer), 191, as seen in FIG. 9. As can be appreciated, at this point second anvil 32 has not yet been attached to anvil shaft 34. Cartridge assembly 128 may be inserted into the subject's intestine through the anus. Cartridge assembly 128 includes a plurality of fasteners for contact with the anvil pockets of anvil assembly 30, but preferably does not include a knife.

Figure 10:
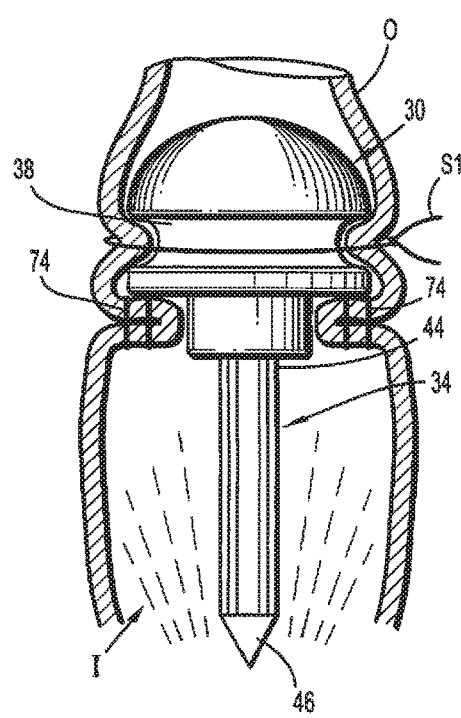
FIG. 10 is a longitudinal cross-sectional view of the tubular organ shown in FIG. 9 during irrigation after the cartridge assembly depicted in FIG. 4A has been removed from the tubular organ.

After operatively coupling cartridge assembly 128 of first surgical instrument 110 (of FIG. 4A) with first anvil assembly 30, the clinician draws a portion of the tubular organ "O" located between first anvil assembly 30 and cartridge assembly 28 toward anvil shaft 34, as illustrated in FIG. 10. To pull said portion of tubular organ "O" toward anvil shaft 34, the clinician wraps a purse string suture "S2" around said portion of tubular organ and then tightens string "S2." The anvil assembly 30 is then approximated toward the cartridge assembly 128 by rotation of an approximation knob (not shown) similar to rotation knob 22 of instrument 10. Subsequently, the clinician actuates a handle assembly (not shown) similar to handle assembly 12 of instrument 10 to eject fasteners 174 stored inside cartridge assembly 128 to fasten the portion of tubular organ pulled with string "S2." Upon actuation of the handle assembly (similar to handle assembly 12 of FIG. 1), fasteners 174 are ejected from cartridge assembly 128 and move toward first anvil assembly 30, penetrating the portion of the tubular organ located between cartridge assembly 128 and first anvil assembly 30. When fasteners 174 reach pockets 41 on proximal surface 42 of first anvil assembly 30, fasteners 174 deform and fasten the portion of the tubular organ "O" located between cartridge assembly 128 and first anvil assembly 30. The clinician then moves end effector 16 back to the open position (e.g., by rotating the approximation knob in the opposite direction), disengages cartridge assembly 128 from anvil shaft 34 by separating shaft 191 from anvil shaft 34, and removes cartridge assembly 128 from tubular organ "O" and instrument 110 from the patient's body, leaving first anvil assembly 30 inside tubular organ "O." Tubular organ "0" may then be irrigated to clear said section from debris and tumor cells, as schematically shown in FIG. 10 by dashed lines "I." In one exemplary process, the clinician irrigates the anorectal canal with water or a saline solution.

Next, the clinician inserts second anvil assembly 32 into tubular organ "O" and slides second anvil assembly 32 over anvil shaft 34, as shown in FIGS. 11 and 12. Second anvil assembly 32 may be inserted, for example, through the subject's anus. Longitudinal keys 48 guide the placement of second anvil assembly 32 along anvil shaft 34. The clinician then inserts cartridge assembly 28 of a second surgical instrument 10 (shown e.g. in FIGS. 1 and 4) containing a cutting device 62 into the tubular organ "O." This cartridge assembly 28 may be similar to the cartridge assembly 128 that was inserted previously except cartridge assembly 28 has a cutting device 62 capable of moving independently of the fasteners. Alternatively, the clinician may insert a cartridge assembly 28 different from the cartridge assembly 128 inserted previously. In any case, the clinician may insert cartridge assembly 28 through the subject's anus. Cartridge assembly 28 is advanced through tubular organ "O" until cartridge assembly 28 operatively engages anvil shaft 34 (FIG. 13) due to the engagement of rod 191. It should be appreciated that instead of using two separate instruments 10, 110, it is also contemplated that the instrument can be provided with a removable cartridge so that the same instrument can be used to fire fasteners 174 and fasteners 74, with a first cartridge for firing fasteners 174 not having a knife and after use, it is removed and replaced with a second cartridge for firing fasteners 74 and having a knife.

After operatively coupling the second instrument 10 with anvil shaft 34, the clinician draws a portion of tubular organ "O" located between first anvil assembly 30 and second anvil assembly 32 toward anvil shaft 34. To pull said portion of tubular organ "O," the clinician may wrap a purse string suture "S3" around said portion of tubular organ "O" and then tightens string "S3" (FIG. 13) to draw the portion of tubular organ located between first anvil assembly 30 and second anvil assembly 32 toward anvil shaft 34. A portion of tubular organ "O" located between second anvil assembly 32 and cartridge assembly 28 is pulled toward anvil shaft 34. In one exemplary method, the clinician wraps a purse string suture "S4" (FIG. 13) around said portion of tubular organ "O" and tightens string "S4" to draw the portion of tubular organ "O" located between second anvil assembly 32 and cartridge assembly 28 toward anvil shaft 34. Thereafter, the clinician rotates approximation knob 22 to move end effector 16 to the approximated position, e.g. approximate anvil assembly 30 and cartridge 28, thereby clamping portions of tubular organ "O." Then, the clinician actuates handle assembly 12 to eject fasteners 80 housed in cartridge assembly 28 and to move cutting device 62 from the retracted position to the deployed position, as depicted in FIG. 7. Fasteners 80 may move sequentially or concomitantly with cutting device 62.

Upon actuation of handle assembly 12, fasteners 80 pass through the portion of the tubular organ located between cartridge assembly 28 and second anvil assembly 32 and reach proximal surface 70 of ring 52. When fasteners 80 reach the pockets 71 of proximal surface 70, fasteners 80 deform and seal the portion of tubular portion located between cartridge assembly 28 and second anvil assembly 32.

While cutting device 62 moves from the retracted position to the deployed position, cutting device 62 passes through annular space 66 and breaks through weakened portion 68 of second anvil assembly 32 to reach tubular member 50 of first anvil assembly 30. After breaking weakened portion 68 of second anvil assembly 32 (FIG. 14), cutting device 62 cuts the portion of the tubular organ "O" located between first anvil assembly 30 and second anvil assembly 32. When cutting device 62 engages tubular member 40, cutting device 62 may urge tubular member 40 distally against the influence of the biasing member 99 of first anvil assembly 30. It is envisioned that cutting device 62 cuts the portion of tubular organ "O" containing the tumor.

Figure 15:
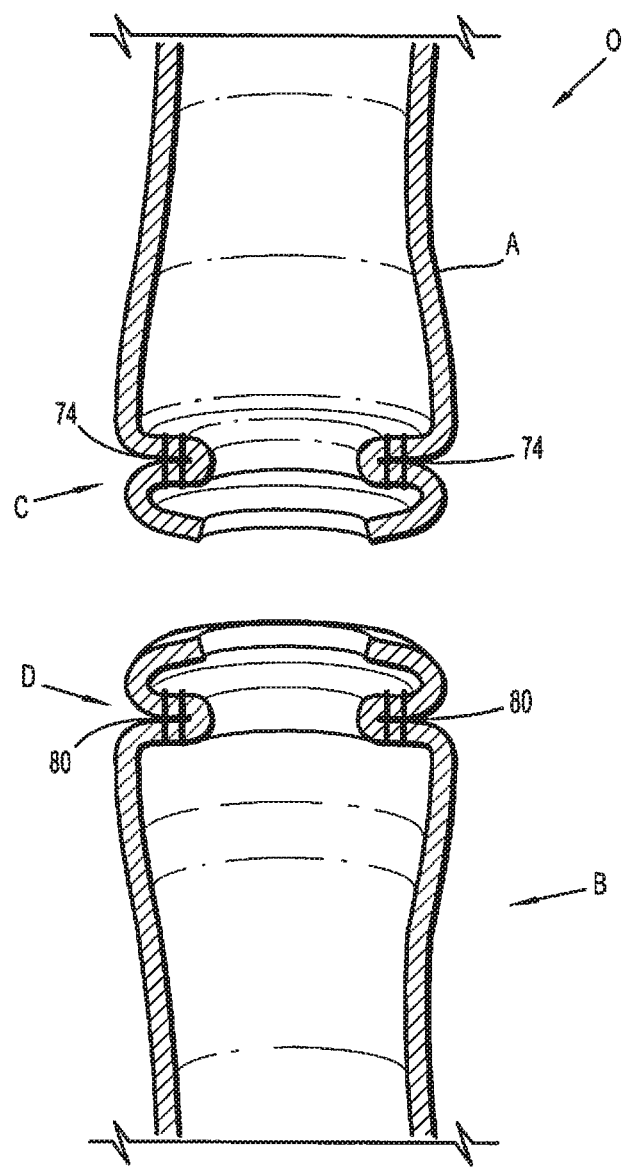
FIG. 15 is a longitudinal cross-sectional view of the tubular organ shown in FIG. 9 after the surgical instrument has been fired and removed from the tubular organ.

Finally, the clinician moves end effector 16 to the open position by rotating approximation knob 22 and removes cartridge assembly 28, first anvil assembly 30, and second anvil assembly 32 from tubular organ "O." Any loose sections of second anvil assembly 32 may be removed individually or may pass through the body. After completing the surgical procedure, tubular organ "O" has been cut in two sections A and B with sealed edges C and D, as seen in FIG. 15.

Thereafter, a circular anastomosis instrument can be inserted through the lower tissue portion and into the tubular organ O. The instrument is clamped to approximate the two portions (since a tissue portion in between has been removed) and then staples are fired to join the portions.

Thus, as can be appreciated, one use of the instrument is in a lower anterior resection procedure. Clamping of the tissue organ O above the intended resection area enables wash out (cleaning out) of the area below the clamping, with stapling occurring below the clamping. This is achieved with access through the anus of the patient.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

What is claimed is:

1. A method of performing a surgical procedure, comprising:
    positioning a first anvil assembly into a tubular organ, the first anvil assembly including an anvil shaft;
    securing the first anvil assembly within the tubular organ;
    inserting a surgical instrument into the tubular organ such that a first cartridge assembly of the surgical instrument operatively associates with the first anvil assembly;
    approximating the first anvil assembly and the first cartridge assembly;
    ejecting a first fastener from the first cartridge assembly toward the first anvil assembly; and
    removing the surgical instrument from the tubular organ such that first cartridge assembly disengages from the first anvil assembly and the first anvil assembly remains secured within the tubular organ.

2. The method according to claim 1, wherein securing the first anvil assembly within the tubular organ includes positioning a first purse string around a first portion of the tubular organ and the first anvil assembly.

3. The method according to claim 2, further comprising drawing a second portion of the tubular organ located between the first anvil assembly and the first cartridge assembly towards the anvil shaft, wherein drawing the second portion of the tubular organ includes positioning a second purse string around the second portion of the tubular organ prior to approximating the first anvil assembly and the first cartridge assembly.

4. The method according to claim 1, further comprising inserting a second anvil assembly into the tubular organ such that the second anvil assembly engages the anvil shaft of the first anvil assembly and is positioned proximally of the first anvil assembly.

5. The method according to claim 4, further comprising inserting the surgical instrument into the tubular organ such that a second cartridge assembly of the surgical instrument engages the anvil shaft of the first anvil assembly and is positioned proximally of the second anvil assembly.

6. The method according to claim 5, further comprising approximating the second cartridge assembly of the surgical instrument and the second anvil assembly, and ejecting a second fastener from the second cartridge assembly toward the second anvil assembly.

7. The method according to claim 6, further comprising cutting a portion of the tubular organ located between the first anvil assembly and the second anvil assembly.

8. The method according to claim 7, wherein cutting the portion of the tubular organ includes firing a knife of the second cartridge assembly into the tubular organ to move the knife from a proximal position towards a distal position.

9. The method according to claim 8, wherein firing the knife of the second cartridge assembly includes passing the knife through a portion of the second anvil assembly into contact with the portion of the tubular organ located between the first anvil assembly and the second anvil assembly.

10. The method according to claim 9, wherein passing the knife through the portion of the second anvil assembly includes breaking through a weakened section of the portion of the second anvil assembly when the knife moves from the proximal position towards the distal position.

11. The method according to claim 6, wherein the first anvil assembly and the second anvil assembly each includes at least one anvil pocket configured to deform the first fastener and the second fastener fired from the first cartridge assembly and the second cartridge assembly, respectively.

12. The method according to claim 5, further comprising drawing a fourth portion of the tubular organ located between the second anvil assembly and the second cartridge assembly of the surgical instrument towards the anvil shaft, wherein drawing the fourth portion of the tubular organ includes positioning a fourth purse string around the fourth portion of the tubular organ.

13. The method according to claim 4, further comprising drawing a third portion of the tubular organ located between the first anvil assembly and the second anvil assembly towards the anvil shaft, wherein drawing the third portion of the tubular organ includes positioning a third purse string around the third portion of the tubular organ.

14. The method according to claim 4, wherein the anvil shaft defines a longitudinal axis, and wherein the first anvil assembly and the second anvil assembly are longitudinally aligned on the longitudinal axis of the anvil shaft.

15. The method according to claim 1, further comprising irrigating an inner portion of the tubular organ.

* * * * *